(12) United States Patent  
McKinnon et al.

(10) Patent No.: US 6,558,344 B2
(45) Date of Patent: May 6, 2003

(54) WOUND IRRIGATION DEVICE

(75) Inventors: Robert J. McKinnon, Highlands Ranch, CO (US); Dean H. Iwasaki, Denver, CO (US); William Pintarelli, San Jose, CA (US)

(73) Assignee: Westmed, Inc., Denver, CO (US)

( * ) Notice: Subject to any disclaimer, the term of this patent is extended or adjusted under 35 U.S.C. 154(b) by 0 days.

(21) Appl. No.: 09/779,967

(22) Filed: Feb. 9, 2001

(65) Prior Publication Data

US 2002/0111591 A1 Aug. 15, 2002

(51) Int. Cl.[7] ............................................. A61M 35/00
(52) U.S. Cl. ............................. 604/35; 604/39; 604/268
(58) Field of Search ............................ 604/39, 35, 268, 604/289

(56) References Cited

U.S. PATENT DOCUMENTS

| | | |
|---|---|---|
| 724,913 A | 4/1903 | Montgomery |
| 1,934,046 A | 11/1933 | Demarchi .................. 128/215 |
| 4,692,140 A | 9/1987 | Olson ........................... 604/40 |
| 4,769,003 A | 9/1988 | Stamler ....................... 604/39 |
| 4,898,588 A | 2/1990 | Roberts ....................... 604/187 |
| 5,496,290 A * | 3/1996 | Ackerman .................. 604/268 |
| 5,941,859 A * | 8/1999 | Lerman ...................... 604/289 |
| 6,293,929 B1 * | 9/2001 | Smith et al. ................ 604/289 |

* cited by examiner

Primary Examiner—Philippe Derakshani
(74) Attorney, Agent, or Firm—Sheridan Ross P.C.

(57) ABSTRACT

A splash shield for use in wound irrigation is provided. The splash shield includes at least one outlet area located along its rim so that irrigating fluid may flow from the splash shield. The splash shield is preferably oval-shaped with a substantially flat top adjacent to which is a receiver unit. The outlet area can be formed, for example, by contoured portions or by a generally V-shaped opening, each able to define a channel to enable the escape of fluid from the splash shield. The splash shield may be used in tandem with a syringe having a tip that is positioned in the receiver unit. Additionally, a basin can be provided for use during wound irrigation. The basin includes indentations to accommodate placement of a portion of the human body within the basin and an exit portion such that fluid in the basin can move in the basin to the edge of a table, bed, gurney or the like.

23 Claims, 15 Drawing Sheets

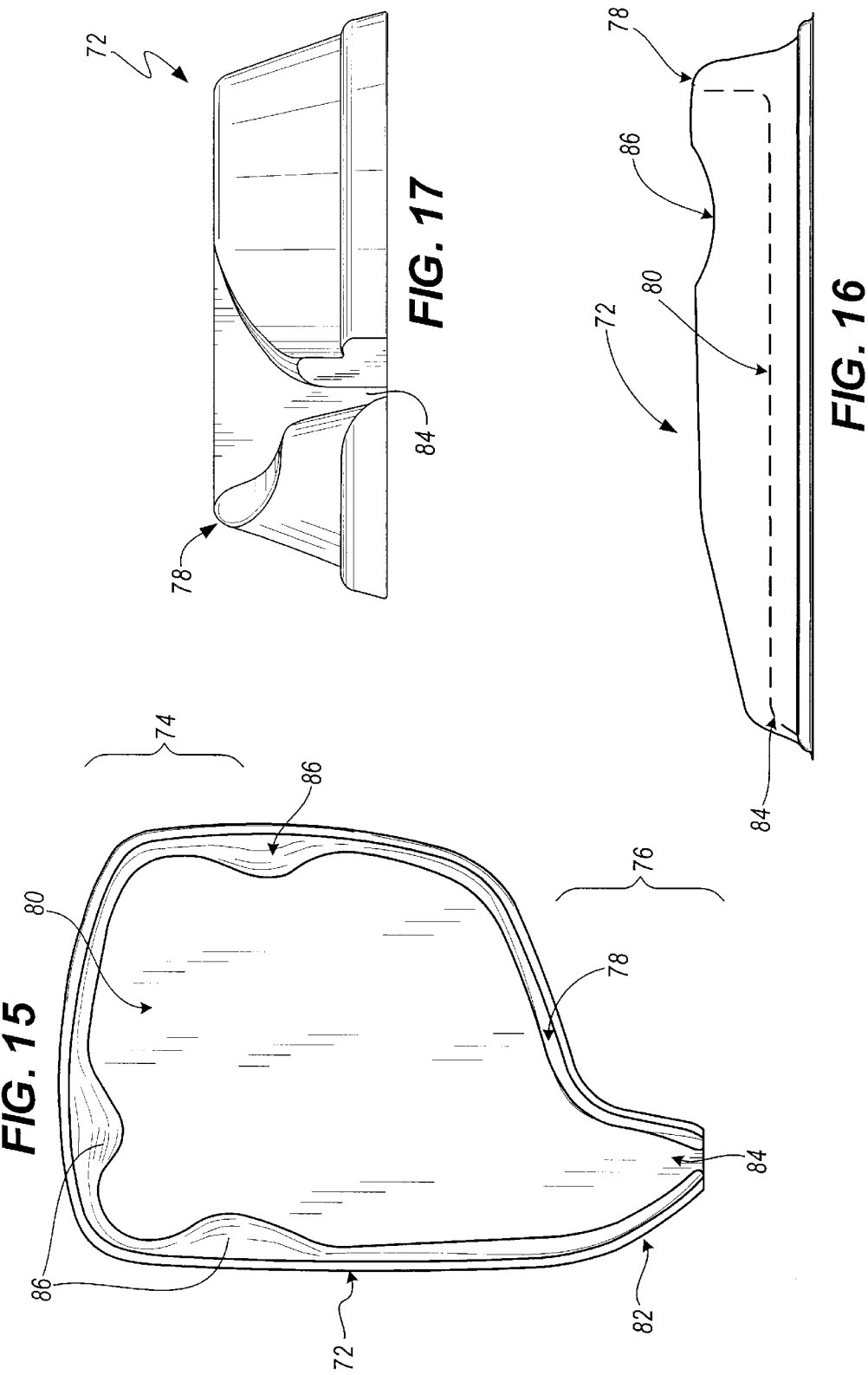

WOUND IRRIGATION DEVICE

FIELD OF THE INVENTION

This invention relates to the field of medical instruments and more particularly to a medical device to prevent splashing of possibly infectious patient bodily fluids and tissues onto medical personnel during wound irrigation.

BACKGROUND OF THE INVENTION

In the medical field, the treatment of lacerations frequently requires that the wound be cleansed prior to closure. This cleansing ensures the removal of any foreign matter such as glass, grass, gravel, dirt, metal particles and/or bacteria. Any and all of these contaminants foster infection if not properly removed from the wound. The cleansing process also removes blood from the wound such that the treating medical personnel may properly explore the wound to verify and complete necessary treatment prior to the closing of the wound.

The above cleansing of a wound is commonly performed by irrigation of the wound using a syringe and a hypodermic needle, or an intravenous catheter with a blunted stylet and where the catheter length has been cut. Typically, the catheter is of 18 gauge size. Typically, the syringe is filled with an irrigating fluid, the needle is directed toward the wound, and the plunger of the syringe is depressed. The irrigation stream from the syringe and catheter combination acts to mechanically dislodge any contaminants from the wound. One obvious drawback of this process is that inherent force of the irrigation stream necessary to cleanse the wound also creates splashing and misting of the irrigation fluid and the contaminated bodily fluid. This splashing increases the risk of infection from the patient to the medical personnel providing treatment.

One known syringe splash shield provides a circular cup with integral tap on the exterior portion for connecting to a standard syringe and integral threads on the interior for attachment of a standard needle hub. The size of the circular cup is such that the needle extends beyond the base plane of the cup. Thus, this design has the inherent disadvantage of being capable of only deflecting high-angle splashes from the wound area. Additionally, the use of a needle that extends beyond the base plane of a cup increases the possibility of stabbing the patient with the needle.

Another known syringe splash shield incorporates a bell-shaped housing for deflecting splashed fluids for use with a syringe but not a needle. While this design avoids the drawback of the aforementioned syringe splash shield with a needle, it too has disadvantages. The open, planar surface of the bell-shaped housing is such that if it is held above the surface of the skin, the housing only contains high-angle splash. As such, this design may fail to fully meet its objective. On the other hand, if the bell-shaped housing is used while contacting the patient, the contained fluid cannot escape and may linger in the wound area and frustrate the intended debridement.

Both of the above known syringe splash shields are defined by circular openings. While this shape may be more easily manufactured, they are less conducive to use on long, narrow portions of the body where lacerations often occur, i.e., forearms, biceps, or calves.

In view of these perceived deficiencies in known syringe splash shields, it would be beneficial to provide a splash shield that enables medical personnel to properly clean a wound while containing essentially all splashed irrigating fluid and contaminants. It would also be beneficial to provide a splash shield that allows the contained fluid to escape in a controlled manner. It would be additionally beneficial to provide a splash guard in a shape that would function ideally on all parts of the patient's anatomy where a laceration may occur.

SUMMARY OF THE INVENTION

In accordance with the present invention, a wound irrigation splash shield is disclosed. The wound irrigation splash shield allows medical personnel to properly cleanse a wound while confining the irrigating fluid within the shield. The wound irrigation splash shield of the present invention is intended to be used in contact with a patient's skin in the area surrounding the wound to prevent essentially all splashing of the irrigating fluid and other contaminants onto other parts of the patient's body or the attending medical personnel.

The wound irrigation splash shield of the present invention is essentially an inverted shell having an open bottom bordered by a rim or bottom edge. The top portion of the shell contains an orifice that allows for the irrigating fluid to pass into the center of the shell. The orifice can be positioned along the shell surface to optimize the direction of the irrigating fluid stream toward the wound. The top portion of the shell may take the shape of a truncated shell such that the top portion of the shell is substantially flat. The orifice may be positioned on this flat portion at the top of the shell. Further, the orifice may be centrally located within this flat portion.

The orifice of the splash shield may be designed to accommodate a syringe such that the syringe fits naturally into a receiver adjacent to the orifice. The receiver and/or the syringe may be designed in such a way that the syringe may be fixedly inserted into the receiver and yet remain removable by exerting a small amount of force. In this way, the syringe may be held to the splash shield without external force and yet be easily removed to re-fill the syringe with irrigating fluid as necessary. In fact, the splash shield of the present invention may be packaged, sold, stored, and/or used with the syringe as a set.

The orifice of the splash shield may also accommodate a luer tip of a bottle filled with saline solution or other irrigating fluid. The bottle may include a cap which may be removed from the bottle, e.g., by twisting or snapping. The removal of the cap may expose the luer tip. The luer tip has a similar geometry to the syringe tip. In this way, the luer tip of the bottle may be inserted directly into the orifice of the splash shield. The bottle may have collapsible sides, for example, bellows, such that attending personnel need only to squeeze the bottle to expel the irrigating fluid from the bottle through the luer tip.

The splash shield of the present invention may be shaped so as to be more readily used on long, narrow portions of the patient's body. For example, the shell may be substantially oval-shaped having a lateral dimension and a longitudinal dimension wherein the longitudinal dimension is greater than the lateral dimension. In one embodiment, the longitudinal dimension is at least 1.2 greater than the lateral dimension. The shape of the splash shield of the present invention may also be defined, at least in part, by the height of the splash shield relative to the longitudinal and/or lateral dimensions of the splash shield. In one embodiment of the present invention, the lateral width of the splash shield may be 1.5 times larger than the height of the splash shield. In another embodiment, the lateral width dimension could be about 2 times larger than height of the splash shield.

The bottom of the splash shield is formed with one or more outlet areas through which the combination of irrigating fluid and body fluids and/or tissues can escape for subsequent capture. In one embodiment, the outlet areas are defined using contoured portions. More specifically, the rim of the splash shield may include substantially flat portions and the contoured portions. The flat portions may be planar. The contoured portions can define channels or outlet area portions which allow the expended irrigating fluid to pass from the interior of the shell to the exterior of the shell. The irrigating fluid passing to the exterior of the shell may then be collected in various ways. For example, the fluid may be allowed to flow naturally to a pan or wound basin placed under the patient's body part or may be collected using a suction device. The contoured portions and the associated channels may be further defined in size relative to other dimensions of the splash shield. For example, at least one contoured portion may be positioned on the rim along at least one length of the rim defining the longitudinal dimension. The length of the channel can be greater than one-half the maximum longitudinal dimension. The height of the channel may be less than one-fourth the height of the splash shield. Alternatively, the length of the channel can be less than one-fourth the maximum longitudinal dimension, while the height of the channel may be at least one-third the height of the splash shield. In another embodiment, the outlet area portions include one or more generally V-shaped openings or channels that interrupt the substantially flat, planar bottom portion. Unlike the contoured portions, these generally V-shaped openings are more concentrated in the middle of the longitudinal dimension of the splash shield and the open area portions extend a much greater distance from the bottom portion.

The splash shield may be used in tandem with the wound basin of the present invention. The wound basin is a walled receptacle with a central tray. The walls extend above the central tray to contain fluid deposited in the wound basin. The wound basin may have an exit extension such that the geometry of the basin is elongated in at least one direction. In this way, the fluid deposited within the basin may be directed toward a fluid disposal bucket which may be positioned beyond the treating surface. The exit extension may include an exit canal to allow fluid deposited in the wound basin to be removed from the central tray. At least one indentation, and preferably two or more indentations, may be formed in the walls at selected positions. The indentations are depressions in the wall such that the height of the indentations is less than the height of the wall, yet still extend above the height of the central tray. The width of the indentations may be greater than the typical wall thickness of the wound basin. The indentations allow medical personnel to place a portion of a patient's body within the central tray without causing undue discomfort to the patient, while the basin will still be capable of retaining any fluid deposited within the basin. Multiple indentations may be formed in the wall of the basin in selected positions to accommodate various body parts in various positions.

Based on the foregoing summary, a number of worthwhile aspects of the present invention can be readily identified. A wound irrigation splash shield is provided that contains essentially all irrigating fluid and associated contaminants within the shield. The wound irrigation splash shield of the present invention includes channels along the rim of the splash shield for controlled removal of the spent irrigating fluid and other contaminants. In that regard, the bottom of the splash shield can remain in contact with the body part being irrigated since the irrigating fluid with possible contaminants can escape through the channels while the bottom is in contact with the patient. The wound irrigation splash shield of the present invention may also be formed in a shape that allows the splash shield to be easily used when treating wounds on a long, narrow portion of the patient's body. The wound basin contains fluid deposited within it and directs it to a proper disposal container. Multiple indentations along the walls of the basin allow the containment of the fluid without sacrificing patient comfort. A wound basin with multiple indentations also may provide attending medical personnel more options of placement of a patient's body part within the wound basin depending upon where the wound is in relation to that body part. Moreover, multiple indentations provide treating personnel with a selection of indentations such that obstacles, such as walls or medical devices, may be avoided when delivering the waste fluid to the disposal receptacle.

Additional advantages of the present invention will become readily apparent from the following discussion, particularly when taken together with the accompanying drawings.

BRIEF DESCRIPTION OF THE DRAWINGS

FIG. 15 is a plan view of one embodiment of the wound basin of the present invention ;

FIG. 16 is a side elevation view of the wound basin shown in FIG. 8;

FIG. 17 is a front elevation view of the wound basin shown in FIG. 8;

DETAILED DESCRIPTION

Figure 1:
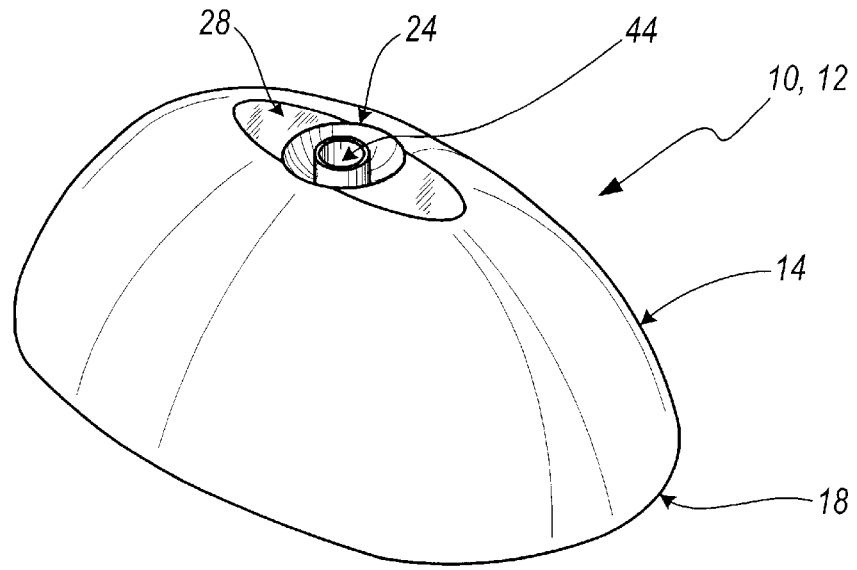
FIG. 1 is a top perspective view of one embodiment of the splash shield of the present invention.
Figure 2:
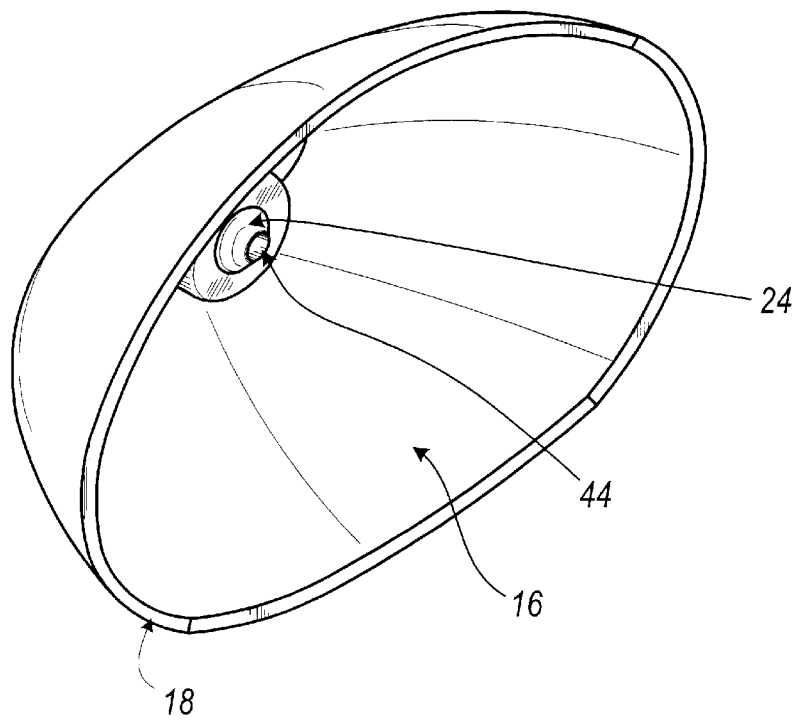
FIG. 2 is a bottom perspective view of the splash shield of FIG. 1.

With reference to FIG. 1 and FIG. 2, a splash shield 10 having a body member 12 with a top 14 and an open bottom 16 is shown. The open bottom 16 of body member 12 defines a bottom rim 18. The bottom rim 18 includes contoured portions 20 and substantially flat portions 22. The body member 12 also includes an irrigating fluid input element 24 that allows irrigating fluid to pass into the body member 12. The irrigating fluid input element 24 may be centrally located along the top 14 of the body member 12. Additionally, a landing, i.e., a substantially flat section, 28 may be formed on the top 14 of the body member 12 adjacent to the irrigating fluid input element 24.

Figure 3A:
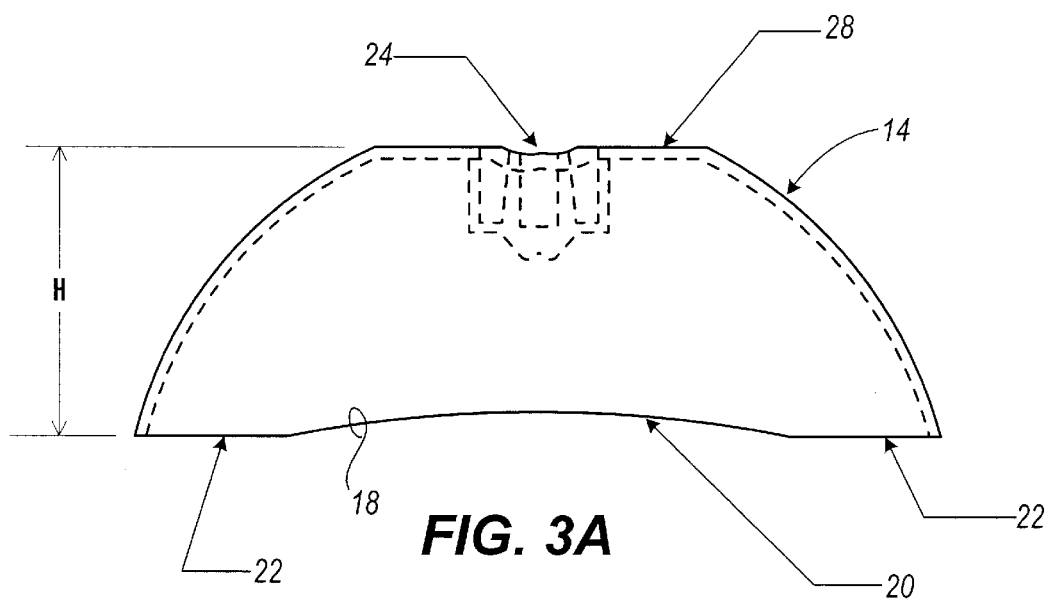
FIG. 3A is an elevation view of the splash shield of FIG. 1.
Figure 3B:
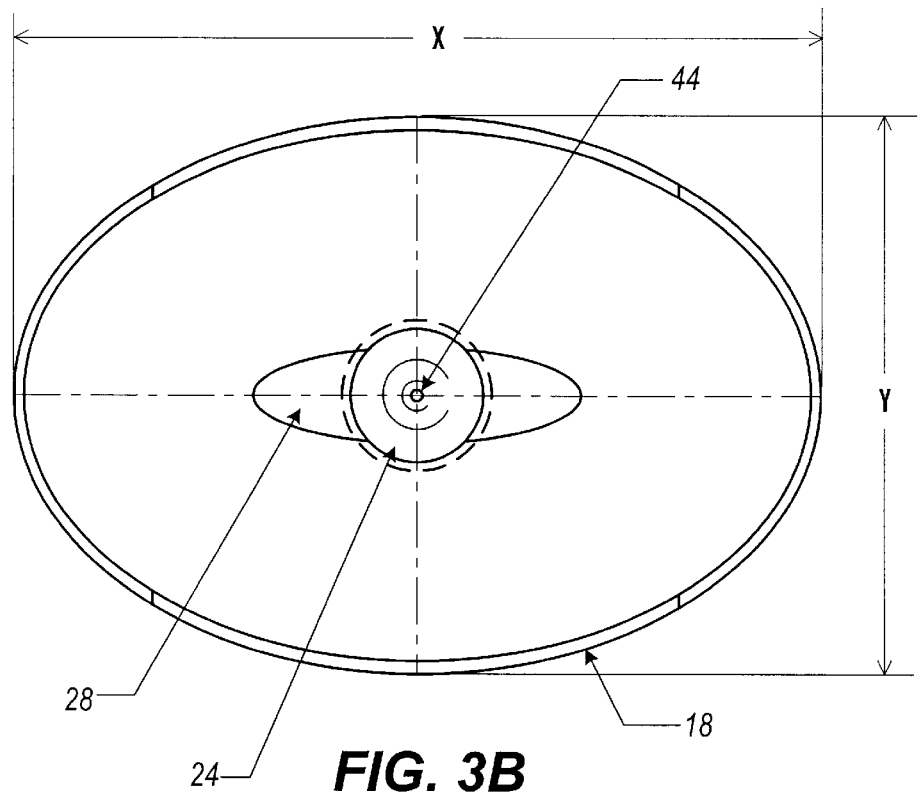
FIG. 3B is a bottom plan view of the splash shield of FIG. 1.

As shown in FIGS. 1 and 2, and more clearly in FIG. 3B, the splash shield body member 12 may be substantially oval-shaped in one embodiment. The body member 12, when oval-shaped, has a maximum longitudinal extent X and a maximum lateral extent Y. The maximum longitudinal extent X and the maximum lateral extent Y are, essentially, the major axis and the minor axis, respectively, of the oval of the bottom rim 18. As seen in FIG. 3A, the body member 12 of this embodiment has a height H defined as the dimension from the substantially flat portions 22 of the bottom rim 18 and the top 14, or the landing 28 if that aspect is included in the embodiment. In one embodiment of the present invention, the maximum longitudinal extent is at least 1.2 times greater than the maximum lateral extent.

Figure 6:
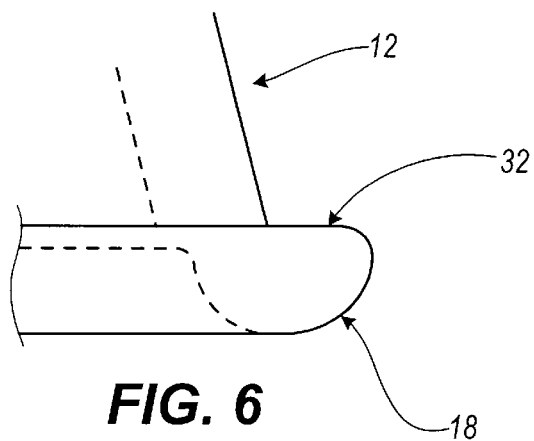
FIG. 6 is an enlarged elevation view of the rim portion of the splash shield of FIG. 4.

As shown in FIG. 3A, the bottom rim 18 has a substantially flat portion 22 and at least one contoured portion 20. In this embodiment, the substantially flat portion 22 lies within a single plane. The contoured portion 20 of the bottom rim 18 lies outside that plane. In this way, the contoured portion 20 of the bottom rim 18 naturally forms a channel 30 with a portion of the patient's body such that irrigating fluid may pass from the interior of the splash shield 10 as shown in FIG. 6.

Figure 4:
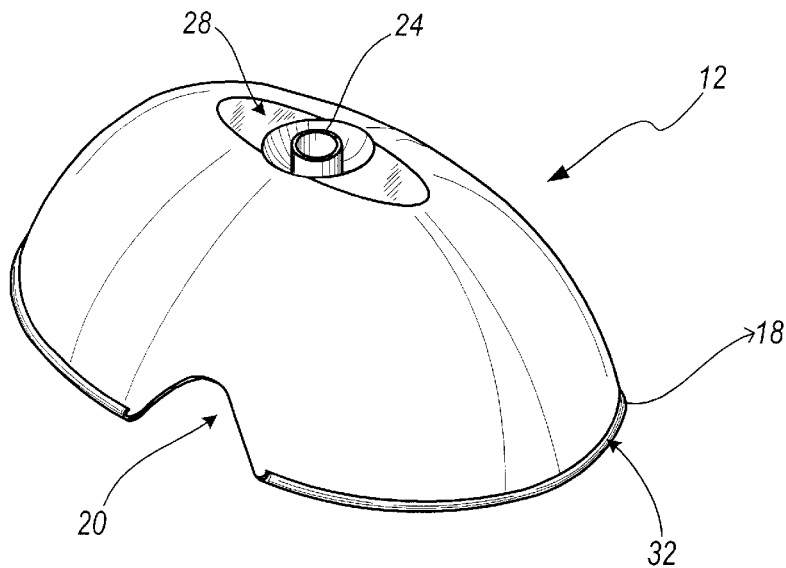
FIG. 4 is a top perspective view of another embodiment of the splash shield of the present invention.
Figure 5:
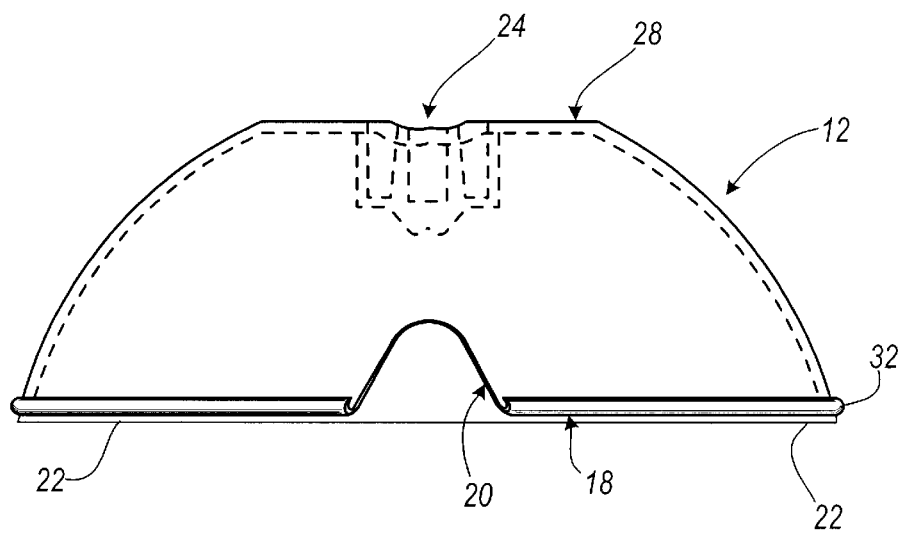
FIG. 5 is an elevation view of the splash shield of FIG. 4.

FIGS. 4 and 5 show an alternative embodiment of the splash shield 12 of the present invention with lip 32 formed along the bottom rim 18. As shown in more detail in FIG. 6, the lip 32 of this embodiment extends outwardly from the open bottom 16, beyond the intersection of the body member 12 and the bottom rim 18. In this embodiment, the bottom surface of the lip 32 is constructed as a radius bounded by the exterior surface of the lip 32 and the interior wall of the body member 12. Additionally, FIGS. 4 and 5 show an alternative geometry of a channel through which spent irrigation fluid exits the splash shield 12. Specifically, a generally V-shaped opening 20 constitutes the contoured portions of the FIG. 1 embodiment. The opening 20 has a maximum height that is at least greater than .1 of the height of the splash shield 10 and, preferably, greater than .15 of the height of the splash shield 10. The lip 32 may be formed around the generally V-shaped opening 20 as well as the bottom rim 18.

Figure 7:
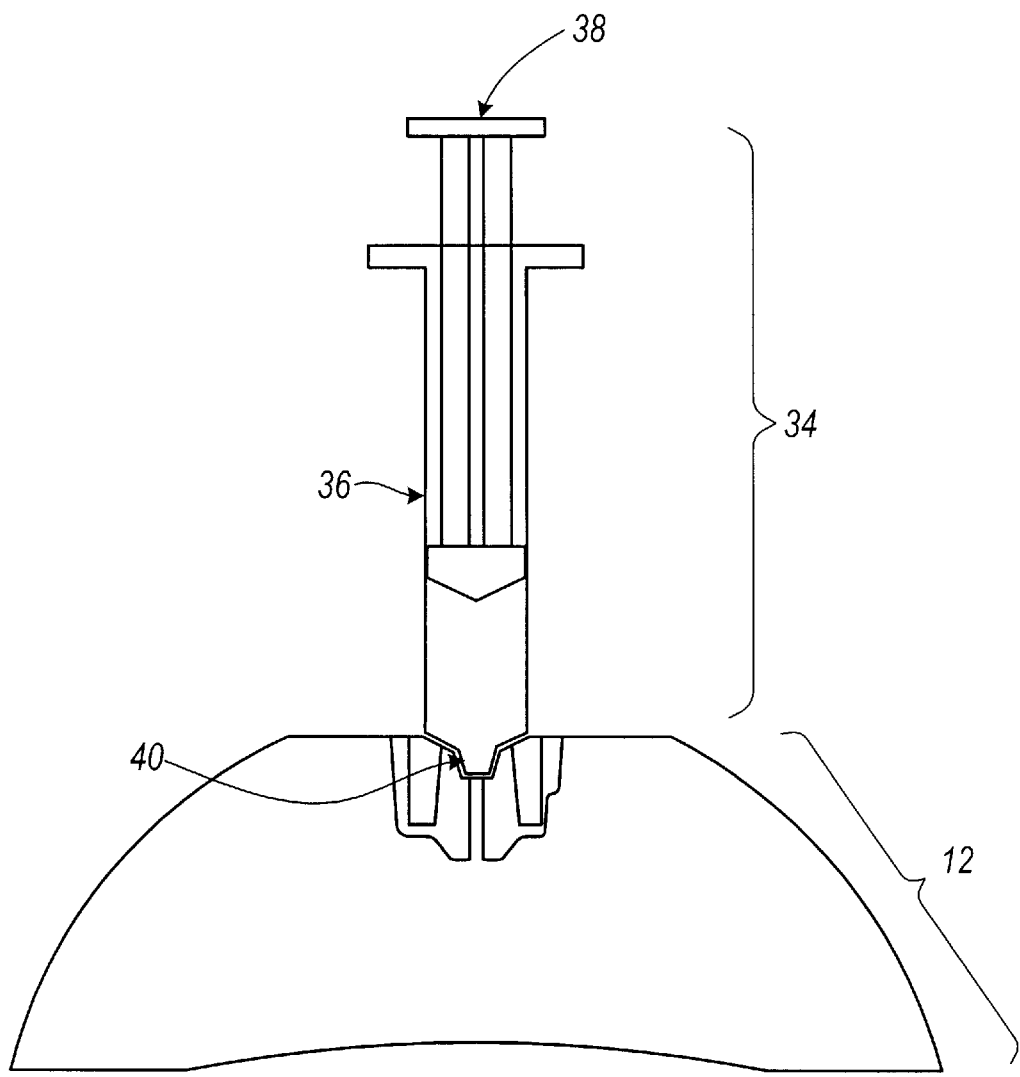
FIG. 7 is an elevation view of one embodiment of the splash shield/syringe combination of the present invention.

With respect to FIG. 7, the wound irrigation device 10 may be embodied by the splash shield 12 and an irrigating fluid supply element 34. The irrigating fluid supply element 34 of this embodiment is shown as a syringe, although other devices could be employed such as a tube that can carry irrigating fluid under pressure or a bottle with a luer tip as described below. The syringe 34 has a syringe body 36, a syringe plunger 38, and a syringe tip 40 with a central syringe channel 42. The size of the syringe tip 40 is selected to be received into bore element 44 of the irrigating fluid input element 24.

Figure 8B:
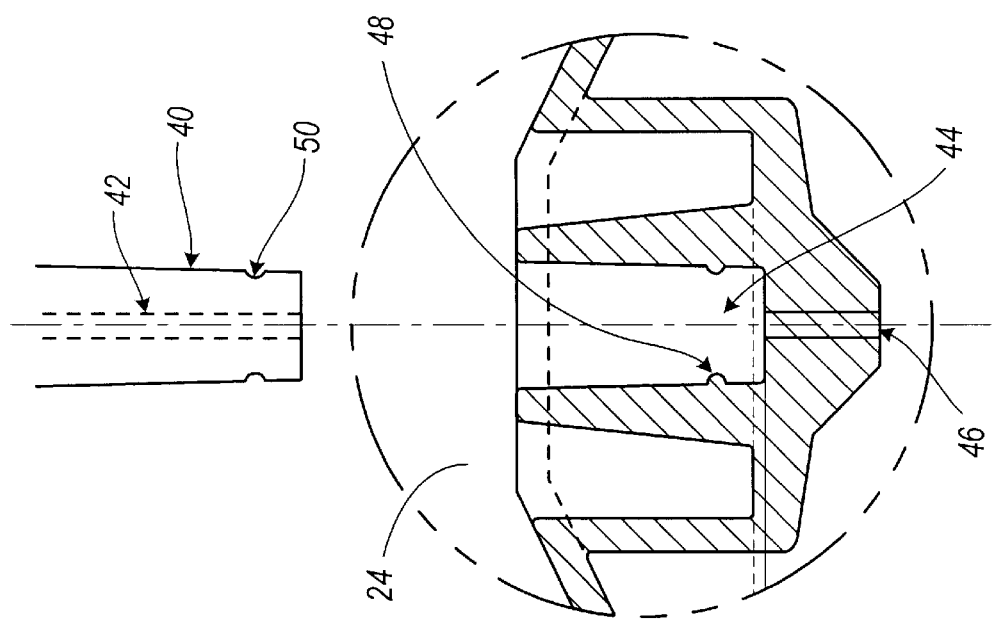
FIG. 8B is an enlarged cross-sectional view of the receiver unit of an alternative embodiment of the splash shield of the present invention.
Figure 8A:
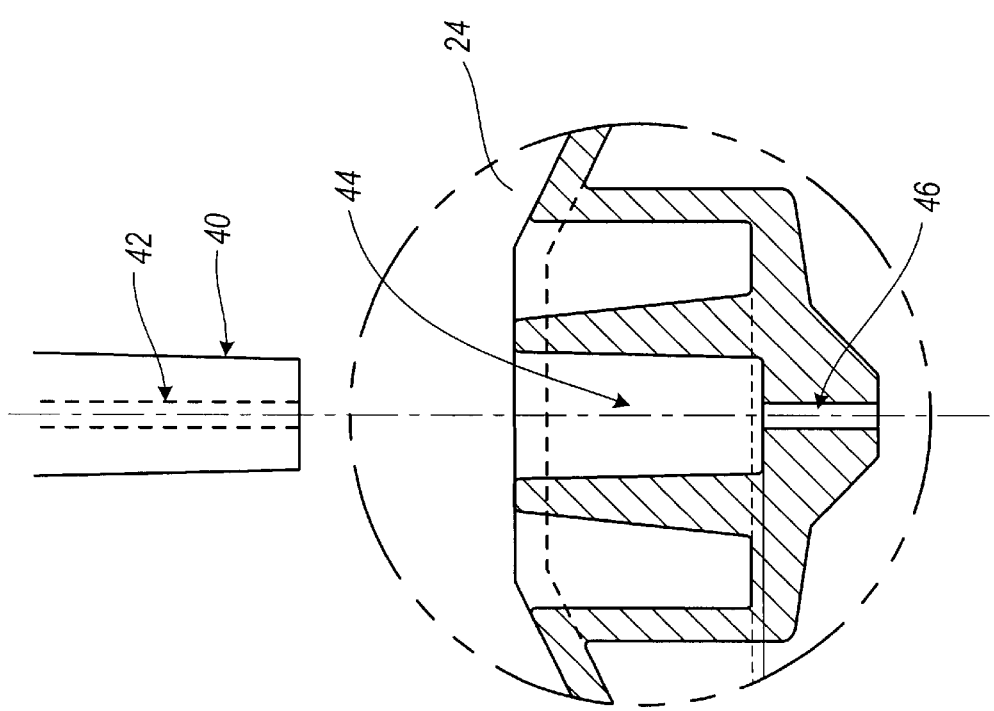
FIG. 8A is an enlarged cross-sectional view of the receiver unit of the splash shield of FIG. 1.

FIG. 8A shows the irrigating fluid input element 24 of the present invention. More particularly, FIG. 8A shows an embodiment of the irrigating fluid input element 24 with a bore element 44 and a constrictor element 46. In this embodiment, the internal wall of the bore element 44 is tapered to mate with the external surface of the syringe tip 40. Thus, the syringe tip 40 may be inserted into the bore element 44. The constrictor element 46 is an orifice, of a smaller diameter than the bore element 44, connecting the bore element 44 to the interior of the body member 12. The smaller diameter of the constrictor element 46 increases the velocity of the irrigating fluid entering the body member 12. Therefore, the force of the irrigating fluid striking the wound is increased.

FIG. 8B shows an alternative embodiment of the bore element 44. In this embodiment, the irrigating fluid input element 24 has a retainer element 48, i.e., a raised portion, along the interior wall of the bore element 44. The retainer element 48 corresponds to a retainer groove 50 on the syringe tip 40. The retainer element 48, when received into the retainer groove 50, may be used to maintain proper insertion of the syringe 24 in the bore element 44. The retainer element 48 may also provide the user with an audible and/or tactile signal indicating proper insertion of the syringe tip 40 into the bore element 44. It is understood that the retainer element 48 may be provided on the syringe tip 40 and the retainer groove 50 may be correspondingly provided along the interior wall of the bore element 44, In operation, the irrigating fluid supply element 34, such as a syringe, is filled with irrigating fluid 52. The syringe 34 may be pre-filled or may be filled when required by placing the syringe tip 40 into a reservoir of irrigating fluid 52 and drawing the syringe plunger 38 distally from the syringe 34. The irrigating fluid 52 may be water, a saline solution or some other antiseptic solution. The syringe tip 40 is inserted into the bore element 44 of the splash shield body member 12. The splash shield 10 is positioned over the wound to be irrigated. It is noted that the positioning of the splash shield 10 over the wound may be done at any time prior to irrigation of the wound, i.e., either before o r after insertion of the syringe 34 into the body member 12.

The irrigating fluid 52 is forced from the syringe 34 by advancing the syringe plunger 38 toward the tip 40 of the syringe 34. Positioning of the splash shield 10 over the wound is necessary to direct the stream 54 of irrigating fluid 52 toward the wound. Once the irrigating fluid 52 is expunged from the syringe 34, the process may be repeated as necessary. To repeat, the syringe 34 is removed from the body member 12, refilled, and reinserted into the body member 12. The irrigating fluid 52 is again forced from the syringe 34.

Figure 9:
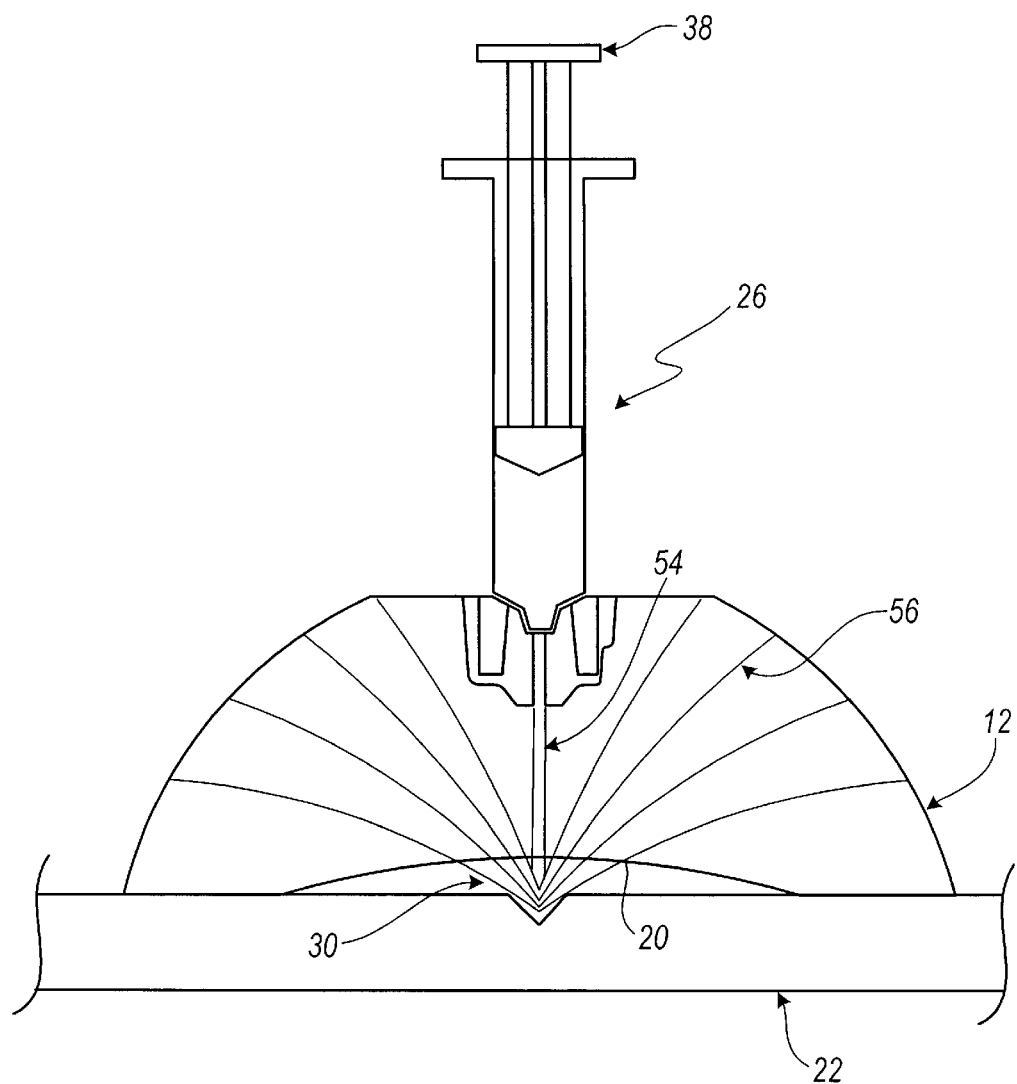
FIG. 9 is an elevation view of the splash shield/syringe combination of FIG. 7.

As shown in FIG. 9, the force of the stream 54 of irrigating fluid 52 will cause at least some portion of the stream 54 to be reflected as splash 56. This splash 56 may be contaminated by material from the wound. The splash 56 is contained within the body member 12 to prevent undesirable contamination of the attending personnel or the patient by the splash material. The contained splash 56 will travel down the interior of the body member 12. The outlet areas, such as the contoured portions or generally V-shaped opening(s) 20, of the splash shield rim 18 form channels between the body member 12 and the patient which allow the contained splash 56 to pass from the body member 12. Because the outlet areas are formed at or adjacent to the bottom portions of the body member 12, the irrigating fluid containing possible contaminants can pass from the splash shield 10 at the same time the bottom portions are in contact with the area of the body being irrigated. The splash 56 exiting the body member 12 through the channels may then be collected in a container for proper disposal.

Figure 10B:
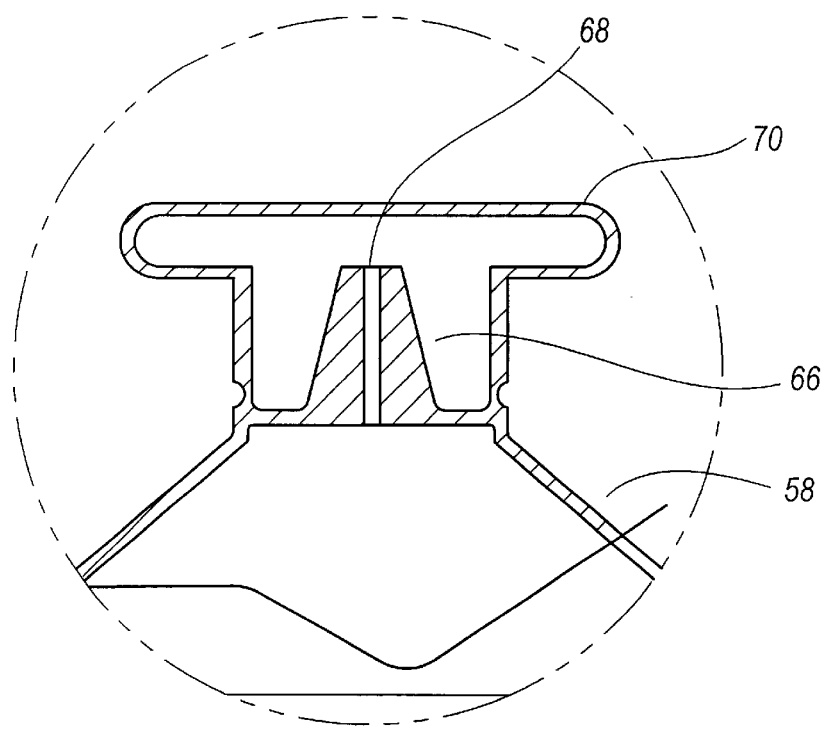
FIG. 10B is an enlarged view of the luer tip portion of the bottle of FIG. 10A.
Figure 10A:
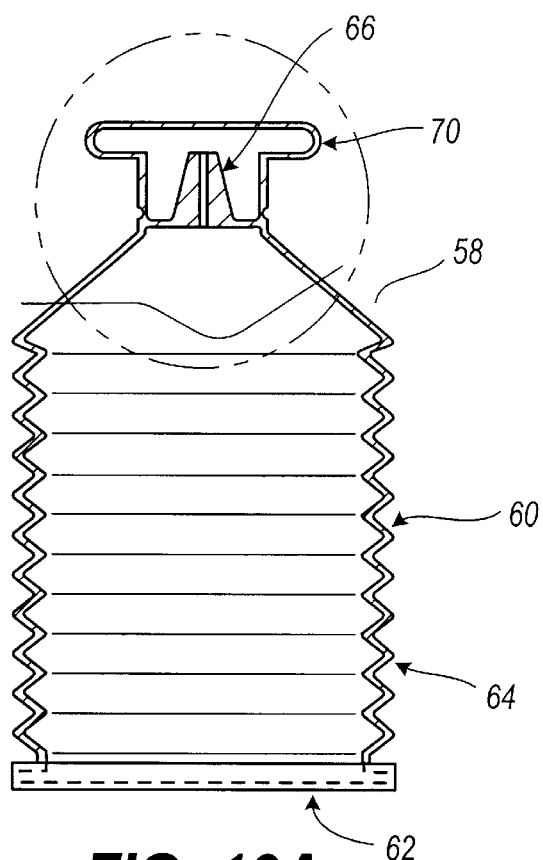
FIG. 10A is an elevation view of the bottle with collapsible sides of the present invention.

With reference to FIG. 10A, a bottle 58 with a collapsible side wall 60 may be used in conjunction with the splash shield 10 of the present invention. In this embodiment, the bottle 58 has a bottom 62, bellows 64 formed in the side wall 60, and a luer tip 66 with a central orifice 68. The bottom 62 should be substantially flat or concave to accommodate storage on a shelf for in a cabinet. The bellows 64 provide the bottle 58 with a collapsible side wall 60. The collapsible side wall 60 allows the attending physician, or other personnel, to expel the irrigating fluid 52 through the central orifice 68 of the luer tip 66 by exerting a pressure on the bottle, e.g., by squeezing the bottle. The luer tip 68 may be protected by a cap 70. The cap 70 may be selectively removed from the bottle 70, and reattached thereto, by twisting or snapping.

As shown in FIG. 10B, the luer tip 66 of the bottle 58 has a similar geometry to the syringe tip 40 including a central orifice 68 for the expulsion of irrigation fluid 52 from the bottle 58.

Figure 11A:
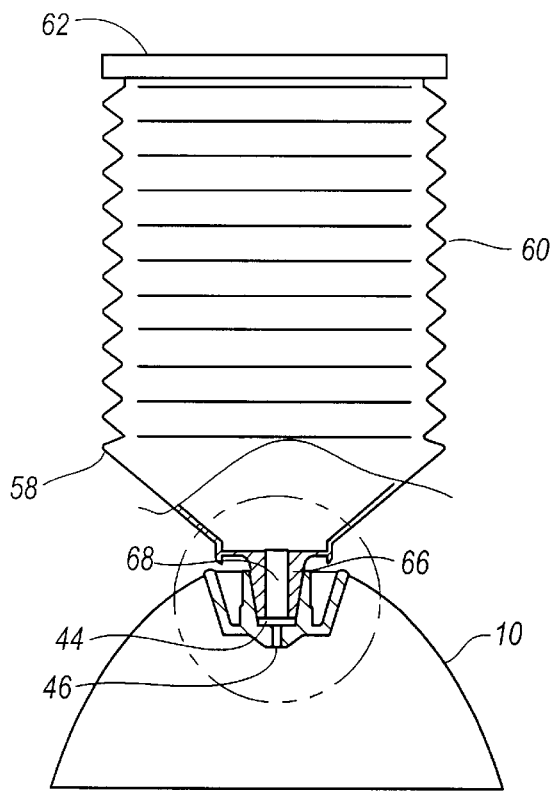
FIG. 11A is an elevation view of one embodiment of the bottle with collapsible sides of the present invention shown in application with an embodiment of the splash shield.

With reference to FIG. 11A, one embodiment of the bottle 58 of the present invention is shown in application with the syringe shield 10. In this embodiment, the luer tip 66 of the bottle 58 has a central orifice 68 larger than the constrictor element 46 of the splash shield 10. The smaller diameter of the constrictor element 46 of the splash shield 10 increases the velocity of the irrigation fluid exiting the bore member 44 of the splash shield 10.

Figure 11B:
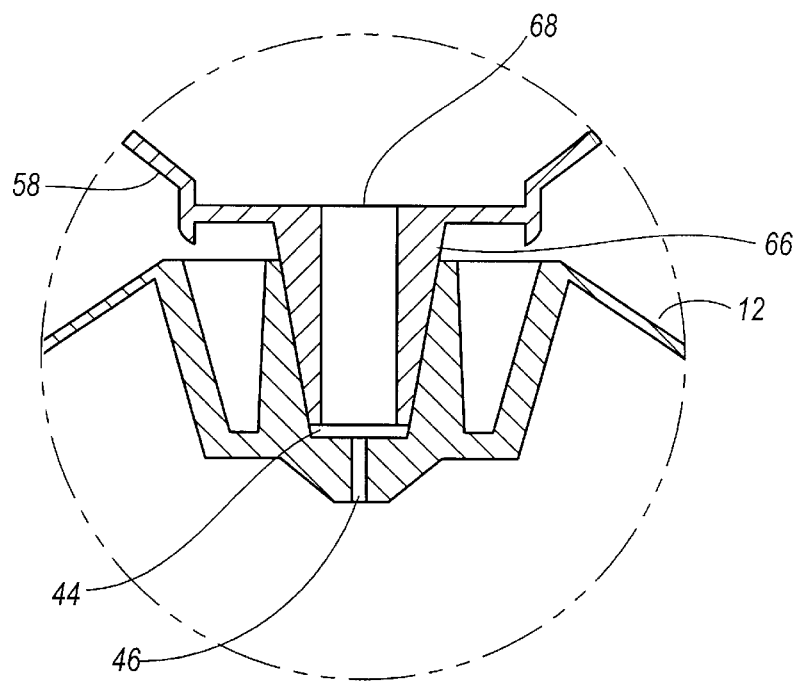
FIG. 11B is an enlarged view of the luer tip portion of the bottle of FIG. 11A.

As shown in FIG. 11B, the luer tip 66 of the bottle 58 and the bore element 44 of the splash shield 10 have mating geometries such that, when the luer tip 66 is properly inserted into the bore element 44 of the splash shield 10, the irrigation fluid 52 is prevented from exiting the bore element 44 of the splash shield 10 other than into the body member 12.

Figure 12A:
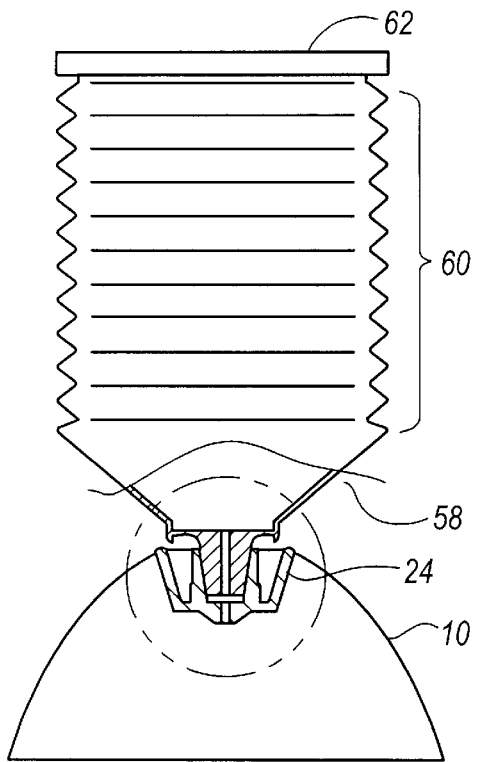
FIG. 12A is an elevation view of an alternative embodiment of the bottle with collapsible sides of the present invention shown in application with an embodiment of the splash shield.
Figure 12B:
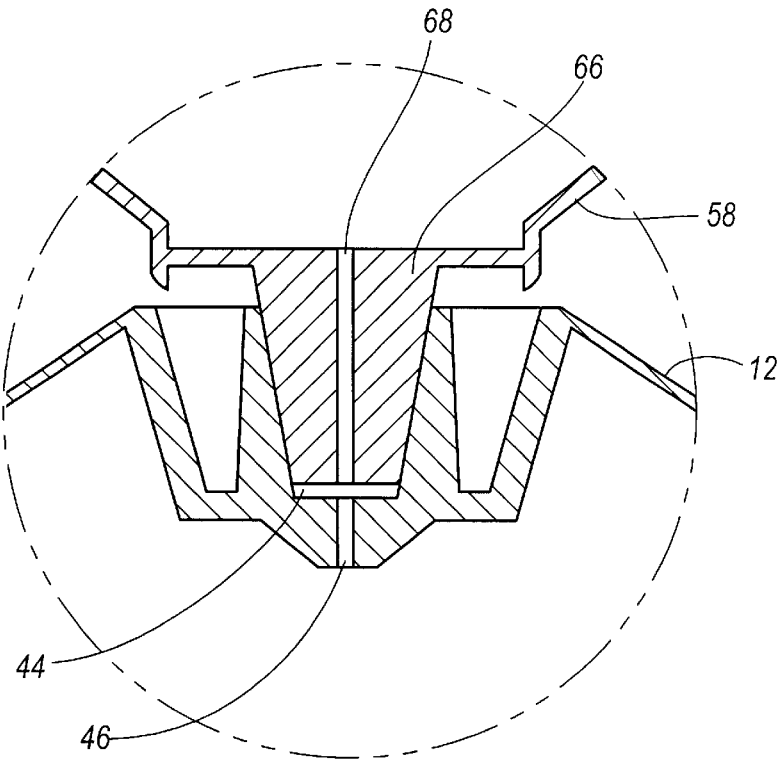
FIG. 12B is an enlarged view of the luer tip portion of the prefilled bottle of FIG. 12A.

With reference to FIG. 12A, a bottle 58 with collapsible side wall 60 is shown with a luer tip 66 having a central orifice 68 or diameter approximately equal to the constrictor element 46 of the bore element 44 of the splash shield 10 of the present invention. As shown in FIG. 12B, again the luer tip 66 of the bottle 58 and the bore element 44 of the splash shield 10 have mating geometries to prevent unwanted leakage of irrigation fluid 52 between these two components. The central orifice 68 of the luer tip 66 of the bottle 58 and the constrictor element 46 of the bore element 44 of the splash shield 10 are substantially in alignment.

In any of the embodiments of the bottle 58 with collapsible side 60, the irrigation fluid 52 can be ejected from the bottle 58 by squeezing or applying pressure to the side 60 or the bottom 62 of the bottle 58. In this way, irrigation fluid 52 is expelled from the bottle 58 through the luer tip 66. When used in conjunction with the splash shield 10, the irrigation fluid 52 is contained within the splash shield 10 and may be collected as described below.

Figure 13:
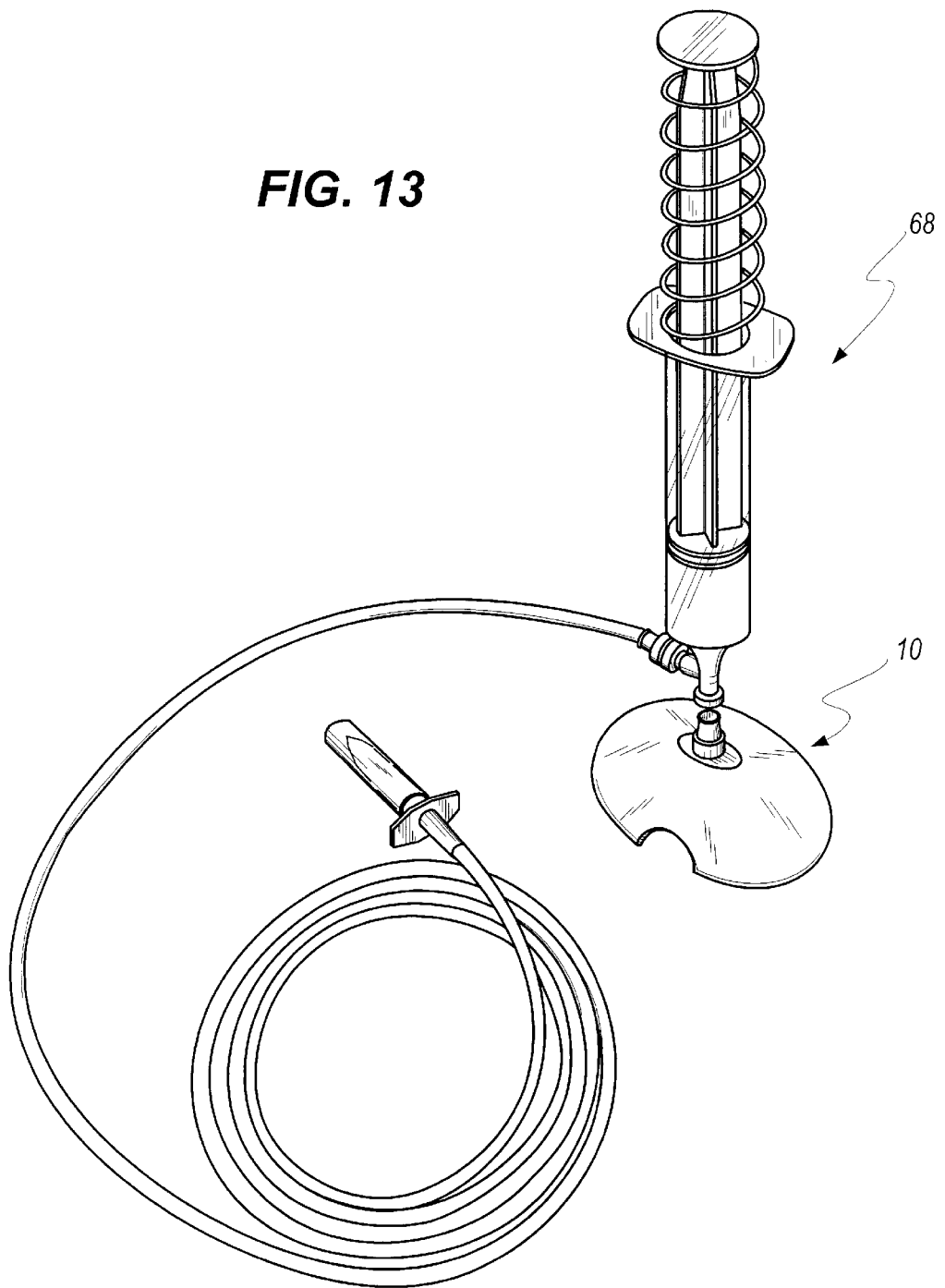
FIG. 13 is a perspective view of another embodiment for supplying irrigating fluid in which an automatic filling irrigation apparatus is operably connected to the splash shield.

Referring next to FIG. 13, another system and methodology are illustrated for supplying irrigating fluid to the splash shield 10. In particular, an automated regaining fluid filling apparatus 68 is shown connected to the splash shield 10. The filling apparatus 68 can be a conventional, commercially available device known to those of skill in the art that has the parts and can operate to automatically receive irrigating fluid for automated supplying thereof to the splash shield 10.

Figure 14:
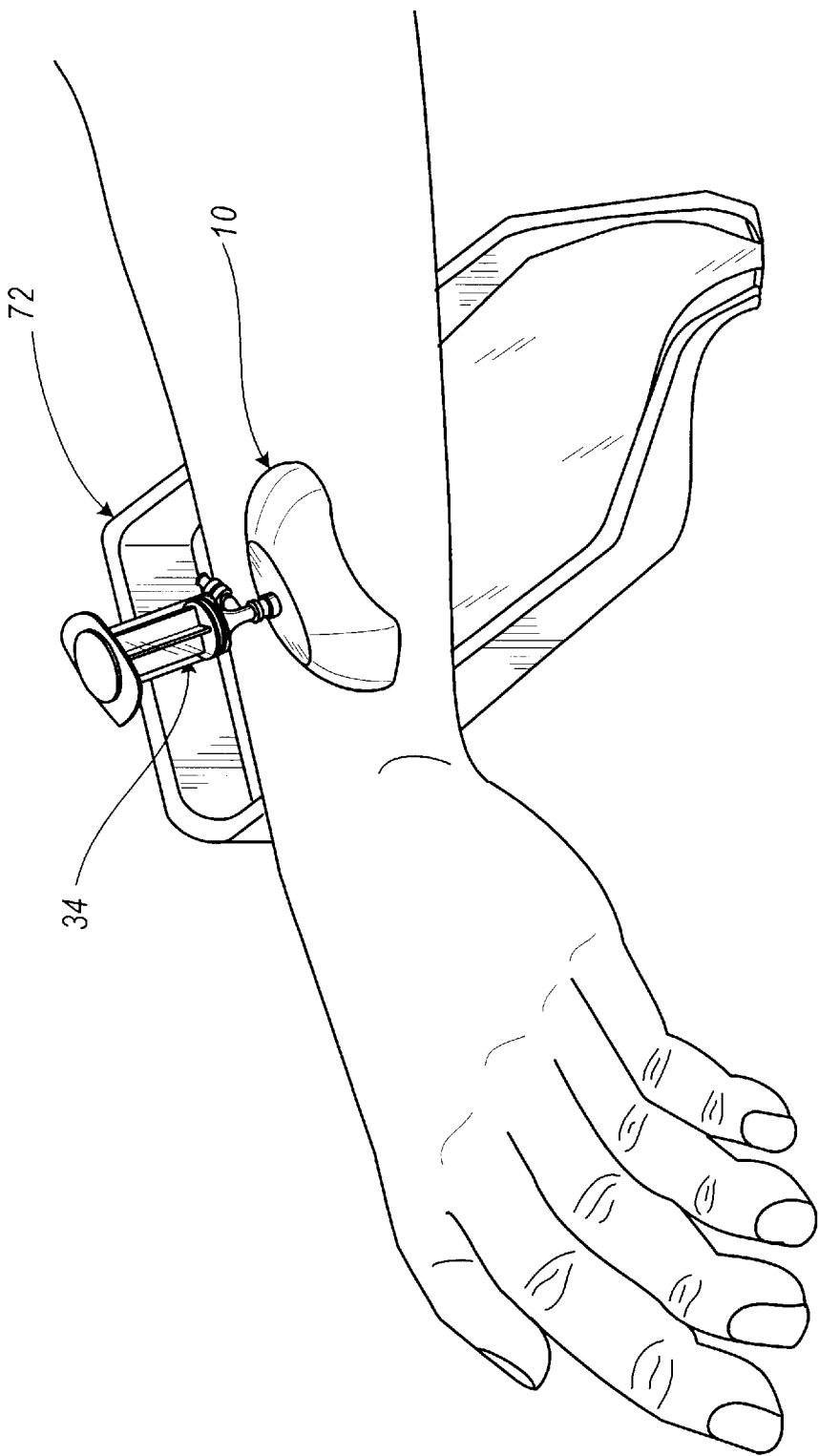
FIG. 14 is a perspective view of the splash shield/syringe combination of FIG. 7 shown in use with a drip pan in the treatment of a patient.

With reference to FIG. 14, a wound basin 72 may be used for collecting the splash 56 exiting the splash shield 10. The wound basin 72 may be a contoured pan. The wound basin 72 provides a vehicle for removing the splash 56 to a desired location to be collected in a final receptacle without leakage or spillage of the splash 56.

One possible embodiment of the basin 72 is shown in FIGS. 15, 16, and 17. The basin 72 is shown having distal end 74, a proximal end 76, an exterior wall 78, a central tray 80, and an exit extension 82 with an exit canal 84 at the proximal end 76 of the basin 72. The central tray 80 may be formed within the basin 72 such that the surface of the central tray 80 slopes from the distal end 74 towards the proximal end 76 of the basin 72. In this way, fluid deposited into the central tray 80 of the basin 72 will naturally flow toward and out of the exit canal 84.

At least one indentation 86 may be formed in the exterior wall 78. The indentation 86 allows a portion of the patient's body to be placed within the central tray 80 for treatment without undue discomfort. When the basin 72 is provided with more than one indentation 86, the indentations 86 may be formed in the exterior wall 78 at positions relative to one another such that the patient's body part is more easily received into the central tray 80. Additionally, the multiple indentations 86 may allow the attending personnel to orient the basin 72 on the treating surface, e.g., a gurney, so that the exit extension 82 extends beyond the treating surface. Thus, any collected fluid may be deposited in a container located off the treating surface, e.g., on the floor. In this way the treating personnel may concentrate on cleansing a wound without using one hand to hold a container.

Figure 18:
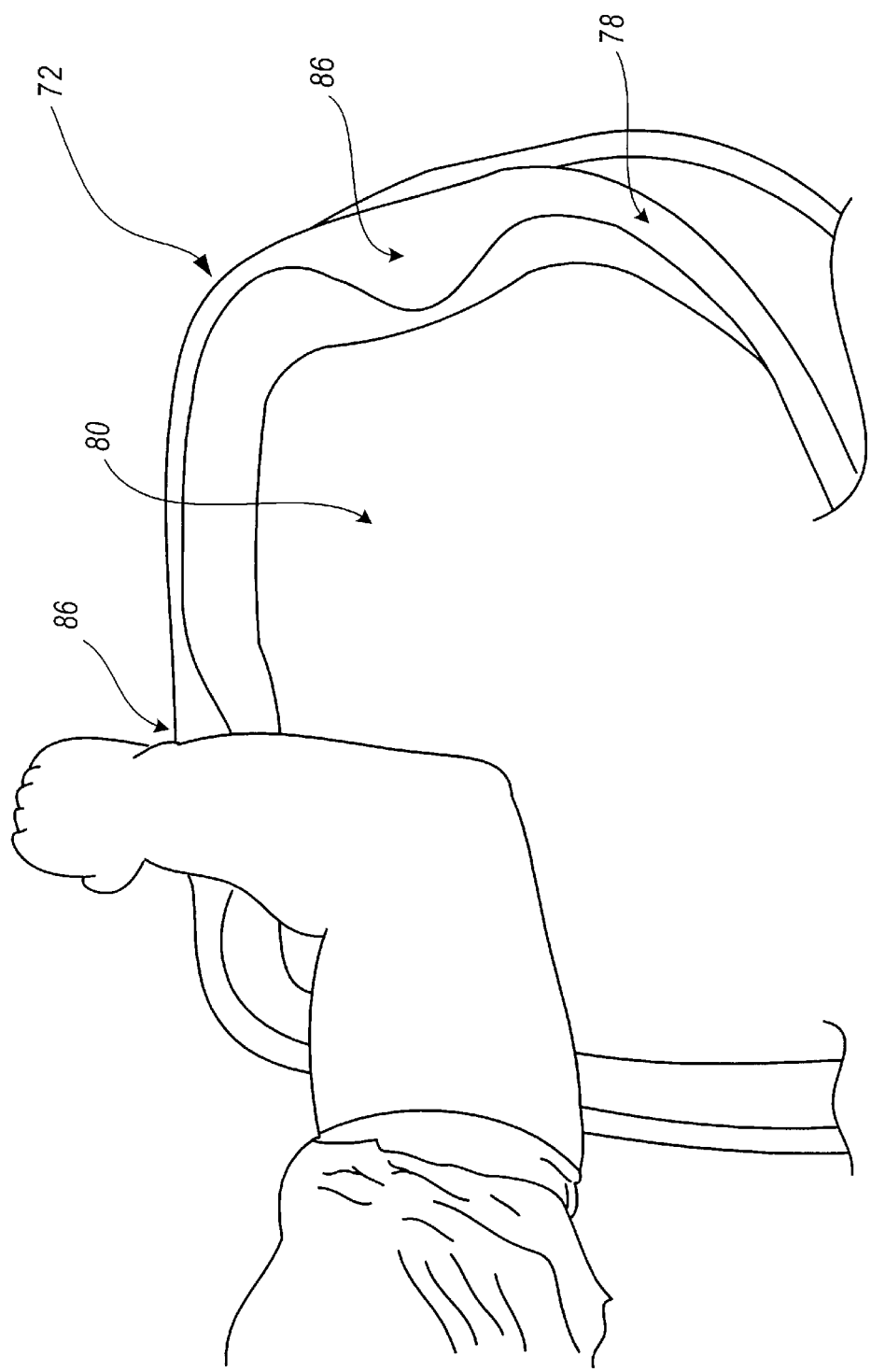
FIG. 18 is a perspective view of the wound basin shown in FIG. 8 in application.
Figure 19:
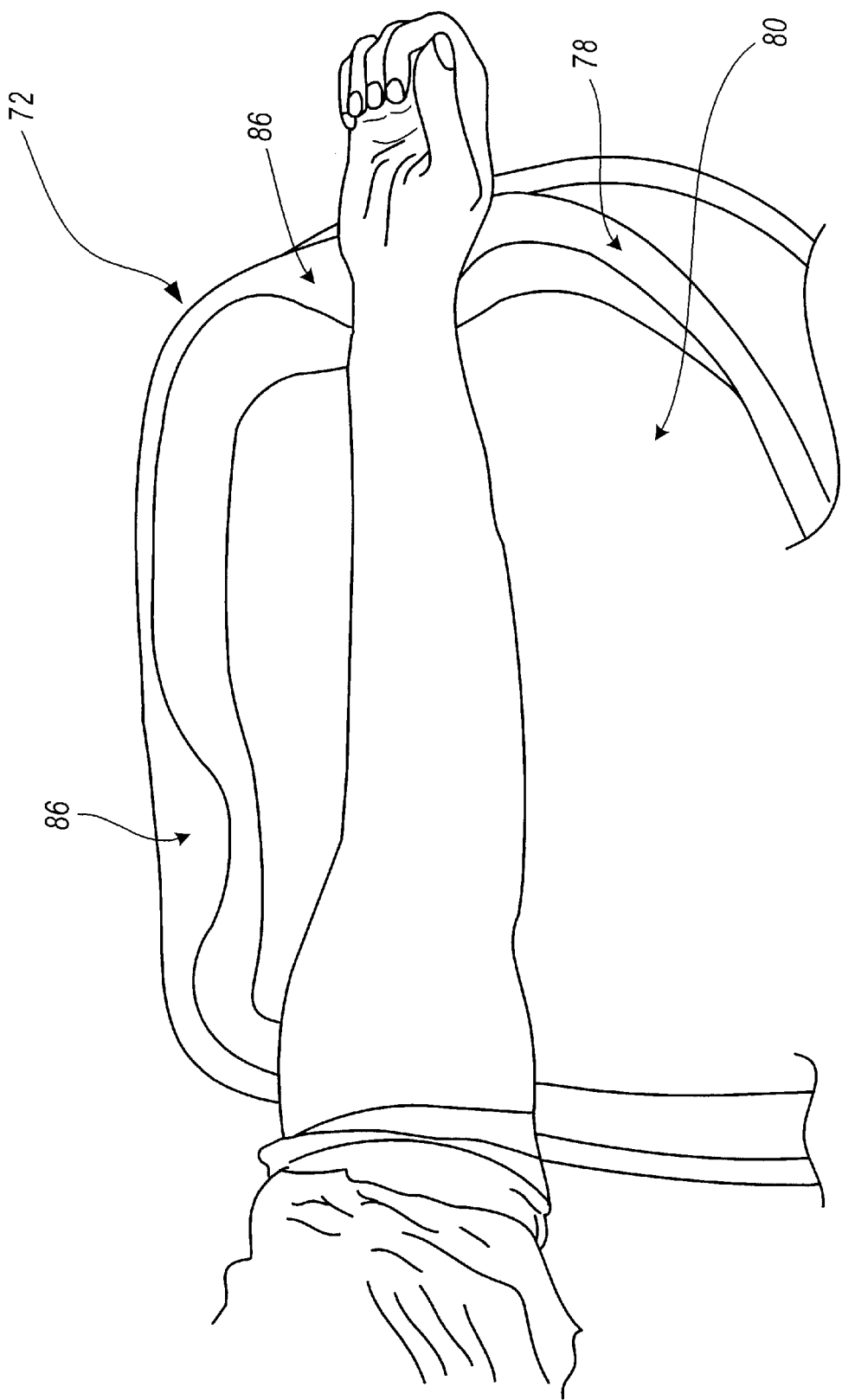
FIG. 19 is a perspective view of the wound basin shown in FIG. 8 in an alternative application.
Figure 20:
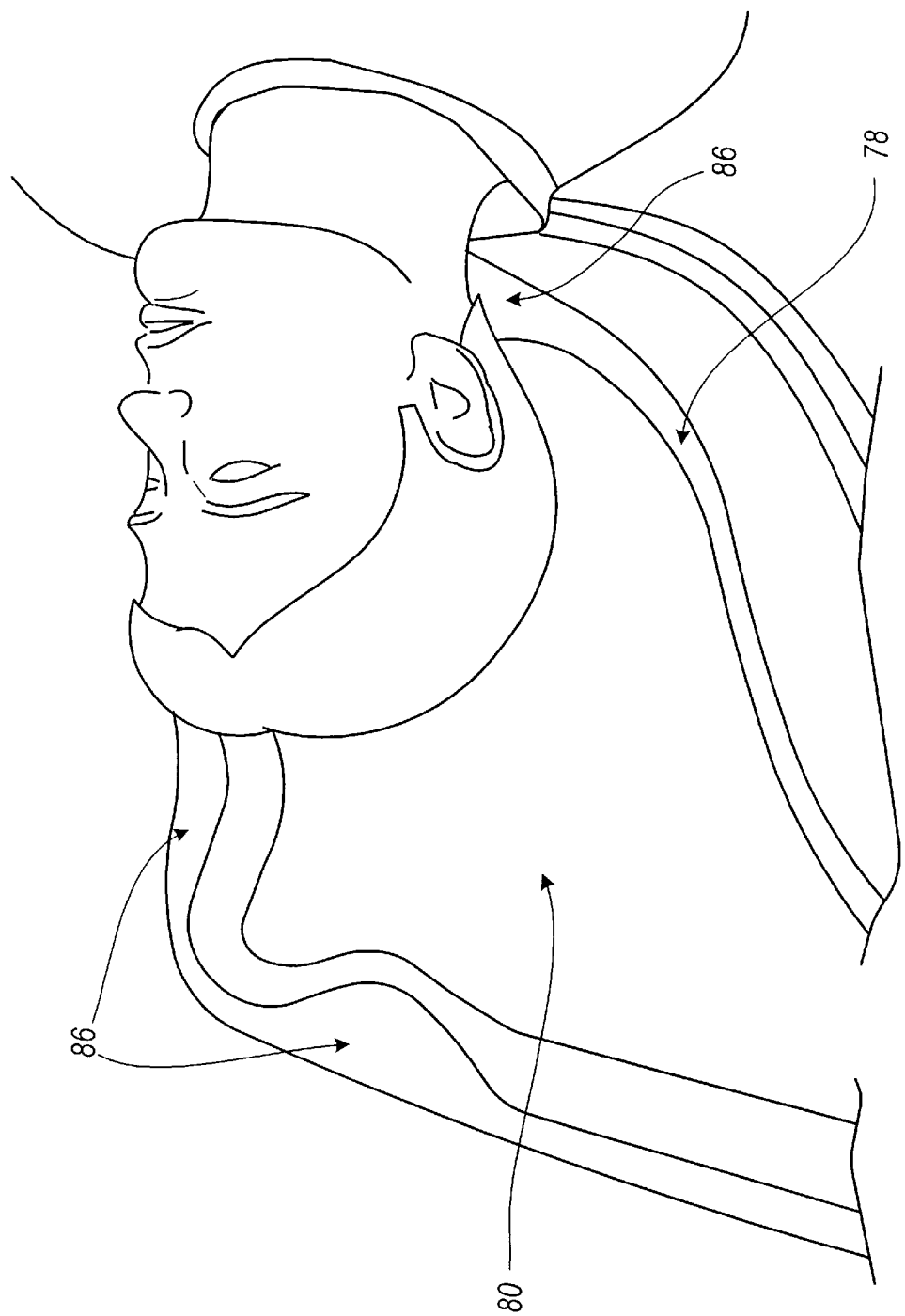
FIG. 20 is a perspective view of the wound basin shown in FIG. 8 in an another alternative application.

FIGS. 18, 19 and 20 show a basin 72 with indentations 86 in possible applications. The indentations 86 may be located in the exterior wall 78 so as to accommodate a variety of body parts of a patient. As shown in FIG. 18, for example, an indentation 86 in the exterior wall 78 along one side and another indentation 86 on the exterior wall 78 at the distal end 74 of the basin 72 may be used to treat a wound on a patient's arm. The patient's arm may be placed in the central tray 80 with the elbow bent such that the forearm rests in one indentation 86 while the upper arm rests in another indentation 86. Similarly, as shown in FIG. 19, a patient's leg, arm, torso or other body part may be placed in the central tray 80 of the basin 72 such that the body part extending beyond the central tray 80 is seated in indentations. 86 on opposite exterior walls 78 of the basin 72.

As shown in FIG. 20, a head wound may be treated by placing the patient's head in the central tray 80 such that the patient's neck rests within an indentation 86. If the basin 72 is provided with multiple indentations 86, the indentation 86 selected to seat the neck may be chosen such that the exit extension 82 of the basin 72 extends beyond the treating surface and to avoid obstacles such as walls or medical equipment. For example, if the treating surface, such as a gurney, is positioned next to a wall, the indentation 86 chosen for placement of the patient's neck may be selected so that the exit extension 82 is located away from the wall, or alternatively, toward the head of the gurney.

Additionally, a liner 88 may be used in connection with the basin 72. The liner 88 can be made in substantially the same form of the basin 72, including all indentations and other contours. The liner 88 can then be placed upon the basin 72, essentially in a stacked position. In this way, the liner 88 may be disposable such that the basin 72 is reusable. The liner can be discarded while the liner 88 may be disinfected and reused. The use of a liner 88 reduces the risk of contamination and therefore, infection control is enhanced.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described herein are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A wound irrigation device, comprising:

a body member having a top and an open bottom, said open bottom including outlet area portions and substantially flat portions integrally formed therewith;

irrigating fluid for delivery to said body member; and an irrigating fluid input element that permits said irrigating fluid to pass into said body member;

wherein at least some portion of said irrigating fluid travels down said interior of said body member and passes outwardly of said body member through said outlet area portions.

2. A device, as claimed in claim 1, wherein:

said body member being substantially oval-shaped having a maximum longitudinal extent and a maximum lateral extent, said maximum longitudinal extent being at least 1.2 times greater than said maximum lateral extent.

3. A device, as claimed in claim 2, wherein:

said body member has a height and said maximum lateral width is at least 1.5 times greater than said height.

4. A device, as claimed in claim 1, wherein:

said body member is substantially curved from said top to said open bottom and said flat portions lie in a plane, said outlet area portions being located outside of said plane of said flat portions.

5. A device, as claimed in claim 1, wherein:

said body member has a maximum longitudinal extent and said outlet area portions include contoured portions that extend along said maximum longitudinal extent greater than one-half of said maximum longitudinal extent.

6. A device, as claimed in claim 1, wherein:

said body member has a maximum longitudinal extent and a height, said outlet area portions include at least one opening that extends less than one-half of said maximum longitudinal extent and extends greater than 0.1 of said height.

7. A device, as claimed in claim 1, wherein:

said top of said body member has a substantially flat section and said irrigating fluid input element includes a bore element recessed relative to said flat section, said bore element for receiving a tip of an irrigating fluid supplying unit.

8. A device, as claimed in claim 7, including in combination therewith:

an irrigating fluid input unit having a tip that is located in said bore element.

9. A device, as claimed in claim 8, wherein:

said irrigating fluid input element further includes a constrictor element, said constrictor element being less in width than said bore element.

10. A wound irrigation device, comprising:

a body member having a top and an open bottom, said body member being substantially oval-shaped with said open bottom having a maximum longitudinal extent and a maximum lateral extent, said body member also having a height, said maximum longitudinal extent being at least 1.2 times greater than said maximum lateral extent and said maximum lateral extent being at least 1.5 times greater than said height, said open bottom having outlet area portions;

an irrigating fluid for delivery to said body member; and an irrigating fluid input element located adjacent said top of said body member that receives said irrigating fluid;

wherein substantially all said irrigating fluid that passes from said body member passes through said outlet area portions.

11. A device, as claimed in claim 10, wherein:

said open bottom includes substantially flat portions integrally formed with said outlet area portions.

12. A device, as claimed in claim 10, wherein:

said maximum lateral extent is about 2.0 times greater than said height.

13. A device, as claimed in claim 10, wherein:

said top of said body member has a substantially flat section and said irrigating fluid input element includes a bore member for receiving a tip of a syringe.

14. A device, as claimed in claim 13, wherein:

said bore member is recessed relative to said flat section.

15. A device, as claimed in claim 10, including in combination therewith:

a basin including a number of walls, a central tray and a plurality of spaced indentations extending from at least one of said walls.

16. A device, as claimed in claim 10, including in combination therewith:

an irrigating fluid supply element selected from the group consisting of: a syringe and a collapsible bottle.

17. A wound basin for use with a wound irrigating device having outlet area portions adjacent to an open end bottom thereof and an irrigating fluid, comprising:

a central tray having portions that receive substantially all said irrigating fluid that passes from said outlet area portions;

a number of walls bounding said central tray; and a plurality of spaced indentations extending inwardly from said walls towards said central tray.

18. A wound basin, as claimed in claim 17, wherein:

said central tray includes a support surface having sloping portions to direct fluid.

19. A wound basin, as claimed in claim 17, wherein:

said plurality of spaced indentations includes three indentations and said number of walls includes first and second side walls and an intermediate wall disposed between said first and second side walls, with one of said indentations extending adjacent to each of said first and second side walls and said intermediate wall.

20. A wound basin, as claimed in claim 17, further including:

a liner disposed over and covering said central tray.

21. A method for irrigating a body part, comprising:

providing a splash shield including outlet area portions adjacent to a bottom end of said splash shield;

connecting an irrigating fluid supply unit to said splash shield;

positioning said splash shield adjacent to the body part wherein at least portions of said bottom end contact portions of the body adjacent to the body part;

delivering irrigating fluid to said splash shield while said portions of said bottom end are in contact with the portions of the body adjacent to the body part; and passing irrigating fluid from said splash shield through said outlet area portions at the same time said portions of said bottom end are in contact with the portions of the body adjacent to the body part.

22. A method, as claimed in claim 21, wherein:

said positioning step is conducted after said connecting step.

23. A method, as claimed in claim 21, wherein:

said outlet area portions interrupt said portions of said bottom end.

* * * * *